US012564540B2

(12) United States Patent  
Droessler

(10) Patent No.: US 12,564,540 B2  
(45) Date of Patent: Mar. 3, 2026

(54) HOLLOW GLASS BODY AND USE OF A HOLLOW GLASS BODY

(71) Applicant: NIPRO CORPORATION, Osaka (JP)

(72) Inventor: Michael Droessler, Gehrden (DE)

(73) Assignee: NIPRO CORPORATION, Osaka (JP)

( * ) Notice: Subject to any disclaimer, the term of this patent is extended or adjusted under 35 U.S.C. 154(b) by 1188 days.

(21) Appl. No.: 17/271,376

(22) PCT Filed: Aug. 29, 2019

(86) PCT No.: PCT/JP2019/033999  
§ 371 (c)(1),  
(2) Date: Feb. 25, 2021

(87) PCT Pub. No.: WO2020/050143  
PCT Pub. Date: Mar. 12, 2020

(65) Prior Publication Data

US 2021/0186810 A1     Jun. 24, 2021

(30) Foreign Application Priority Data

Sep. 3, 2018     (DE) ..................... 10 2018 006 961.4  
Sep. 3, 2018     (DE) ..................... 10 2018 006 968.1

(51) Int. Cl.  
   *A61J 1/06*         (2006.01)  
   *A61J 1/05*         (2006.01)  
         (Continued)

(52) U.S. Cl.  
   CPC ............ *A61J 1/065* (2013.01); *A61M 5/3129* (2013.01); *B23K 26/0622* (2015.10);  
        (Continued)

(58) Field of Classification Search  
   CPC ........... A61J 1/065; A61J 1/05; A61M 1/178;  
                A61M 5/3129; B23K 26/0622;  
        (Continued)

(56) References Cited

U.S. PATENT DOCUMENTS 5,782,815 A * 7/1998 Yanai ...................... A61M 5/28  
                                         604/218  
6,310,318 B1 10/2001 Vetter et al.  
        (Continued)

FOREIGN PATENT DOCUMENTS

DE         19616327        11/1997  
DE         19904978        8/2000  
        (Continued)

OTHER PUBLICATIONS

Wolfram Alpha equation solver. https://www.wolframalpha.com/input?i=B%2FA+%3D+0.95%2C+solve+for+%28A-B%29%2FA+. Accessed Sep. 29, 2025. (Year: 2025).*

(Continued)

*Primary Examiner* — Adam Marcetich  
*Assistant Examiner* — Timothy L Flynn  
(74) *Attorney, Agent, or Firm* — Wenderoth, Lind & Ponack, L.L.P.

(57) ABSTRACT

A hollow glass body includes a cylindrical main body portion having a first inside diameter, and a first end opening and a second end opening on opposite ends of the hollow glass body. The hollow glass body has a second inside diameter at the second end opening. The second inside diameter is smaller than the first inside diameter. A difference between the first inside diameter and the second inside diameter is at most 100 μm.

23 Claims, 12 Drawing Sheets

(51) Int. Cl.

| | |
|---|---|
| *A61M 5/178* | (2006.01) |
| *A61M 5/31* | (2006.01) |
| *B23K 26/0622* | (2014.01) |
| *B23K 26/08* | (2014.01) |
| *B23K 26/38* | (2014.01) |
| *B23K 26/402* | (2014.01) |
| *B65B 3/00* | (2006.01) |
| *C03B 33/02* | (2006.01) |
| *C03B 33/06* | (2006.01) |

(52) U.S. Cl.
CPC .......... *B23K 26/0823* (2013.01); *B23K 26/38* (2013.01); *B23K 26/402* (2013.01); *B65B 3/003* (2013.01); *C03B 33/0222* (2013.01); *C03B 33/06* (2013.01); *A61J 1/05* (2013.01); *A61M 5/178* (2013.01)

(58) Field of Classification Search
CPC .. B23K 26/0823; B23K 26/38; B23K 26/402; B23K 2101/04; B23K 2103/54; B65B 3/003; C03B 33/0222; C03B 33/06
See application file for complete search history.

(56) References Cited

U.S. PATENT DOCUMENTS

| | | | |
|---|---|---|---|
| 2001/0009250 A1 | 7/2001 | Herman et al. | |
| 2001/0035447 A1 | 11/2001 | Gartner et al. | |
| 2010/0076375 A1* | 3/2010 | Alexandre | A61M 5/30 604/69 |
| 2012/0060558 A1 | 3/2012 | Haselhorst et al. | |
| 2014/0216108 A1 | 8/2014 | Wiegel et al. | |
| 2015/0114043 A1 | 4/2015 | Risch et al. | |
| 2015/0140241 A1* | 5/2015 | Hosseini | C03B 33/0222 65/102 |
| 2015/0165548 A1 | 6/2015 | Marjanovic et al. | |
| 2016/0129526 A1 | 5/2016 | Russ et al. | |
| 2016/0272531 A1 | 9/2016 | Inayama | |
| 2017/0216972 A1 | 8/2017 | Pialot et al. | |
| 2018/0029918 A1 | 2/2018 | Hunzinger et al. | |
| 2018/0215648 A1 | 8/2018 | Wada et al. | |
| 2018/0215649 A1 | 8/2018 | Wada et al. | |
| 2019/0051514 A1* | 2/2019 | Vidra | B23K 26/0622 |
| 2019/0210909 A1* | 7/2019 | Wagner | A61M 5/3129 |
| 2021/0229848 A1* | 7/2021 | Nishizawa | B05B 15/65 |

FOREIGN PATENT DOCUMENTS

| | | |
|---|---|---|
| DE | 10 2010 045 094 | 3/2012 |
| DE | 10 2011 006 738 | 10/2012 |
| DE | 10 2012 101 948 | 9/2013 |
| DE | 10 2016 114 104 | 2/2018 |
| EP | 0 723 784 | 6/2003 |
| EP | 3 366 656 | 8/2018 |
| JP | 61-115853 | 6/1986 |
| JP | 2008-249599 | 10/2008 |
| WO | 2008/034960 | 3/2008 |
| WO | 2014/190225 | 11/2014 |

OTHER PUBLICATIONS

Extended European Search Report issued Jun. 30, 2022 in European Patent Application No. 19857556.5.

International Search Report issued Nov. 19, 2019 in International (PCT) Application No. PCT/JP2019/033999.

Extended European Search Report issued May 23, 2022 in corresponding European Patent Application No. 19856918.8.

Notice of Opposition dated Apr. 14, 2025 in European Patent Application No. 19857556.5.

International Standard ISO 13926-1:2004, "Pen systems—Part 1: Glass cylinders for pen-injectors for medical use", Third edition, published on Nov. 1, 2004.

International Standard ISO 11040-4:2015, "Prefilled syringes—Part 4: Glass barrels for injectables and sterilized subassembled syringes ready for filing", Third edition, published on Apr. 1, 2015.

Summons to attend oral proceedings pursuant to Rule 115(1) EPC dated Dec. 19, 2025 in European Patent Application No. 19857556. 5.

\* cited by examiner 101                                102

Fig. 6
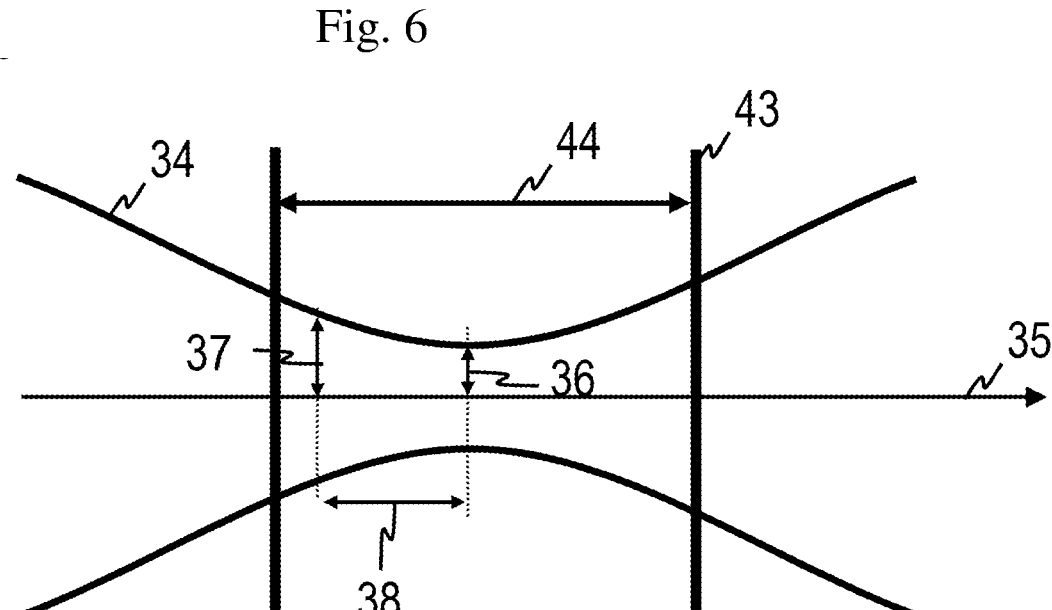
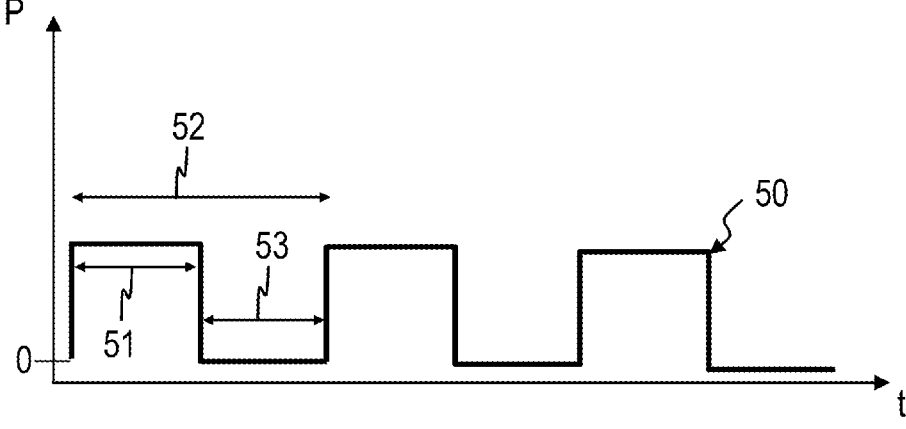
Fig. 7

HOLLOW GLASS BODY AND USE OF A HOLLOW GLASS BODY

TECHNICAL FIELD

The invention relates to a hollow glass body. The invention relates in particular to a hollow glass body that may be used for producing a receptacle. The invention relates in particular to a hollow glass body for medical receptacles such as syringes, medical cartridges, or small bottles. The invention relates in particular to such hollow glass bodies that can be separated from a glass tube by using laser radiation during the production.

BACKGROUND

Hollow glass bodies can be used as medical receptacles such as syringes or drug cartridges or as non-medical receptacles, can be components of such medical receptacles or non-medical receptacles or can serve as an intermediate product in the production of such medical receptacles or non-medical receptacles.

Laser radiation can be used to reshape hollow glass bodies. DE 10 2010 045 094 A1, DE 10 2012 101 948 A1 and DE 10 2016 114 104 A1 describe exemplary methods and systems for laser-assisted reshaping of a glass body.

Laser radiation can also be used to separate hollow glass bodies. DE 10 2011 006 738 A1 describes a method of separating hollow glass, wherein a starting scratch is introduced by means of scratching, the hollow glass is heated by means of laser radiation, subsequently cooled and reheated by means of laser radiation.

Conventional hollow glass bodies that have been separated from a glass tube using laser radiation may show an undesirably large reduction in the inside diameter at the end of the hollow glass body at which the hollow glass body is separated, for example by scratching and subsequent laser-assisted heating in order to introduce mechanical stresses. Such a significant reduction in the inside diameter at an end opening of the hollow glass body can make the further processing by a machine difficult, increase the reject rate during the production process, and reduce reproducibility of the medical receptacles that comprise the hollow glass body or are produced from the hollow glass body.

BRIEF SUMMARY OF THE INVENTION

The problem to be solved by the invention is the provision of an improved hollow glass body for a receptacle. In particular, a problem to be solved by the invention is the provision of a hollow glass body which can be handled more easily by a machine, for example when the hollow glass body is filled and/or closed, wherein the hollow glass body can be separated from a glass tube using laser radiation. In particular, a problem to be solved by the invention is the provision of a hollow glass body which can be produced using manufacturing techniques that have a low reject rate and/or a high reproducibility. In particular, a problem to be solved by the invention is the provision of a hollow glass body which is suitable as a medical or non-medical receptacle, as a component of such a receptacle or as an intermediate product for such a receptacle.

According to the present invention, hollow glass bodies and a use of a hollow glass body having the features recited in the independent claims are provided. The dependent claims define embodiments.

A hollow glass body according to a first embodiment comprises a cylindrical main body portion having a first inside diameter. The hollow glass body comprises first and second end openings at opposite ends of the hollow glass body, wherein the second end opening delimits the cylindrical main body portion and the hollow glass body has a second inside diameter at the second end opening. The second inside diameter may be smaller than the first inside diameter. A difference between the first inside diameter and the second inside diameter may be at most 100 μm.

A hollow glass body according to a second embodiment comprises a cylindrical main body portion having a first inside diameter. The hollow glass body comprises first and second end openings at opposite ends of the hollow glass body, wherein the second end opening delimits the cylindrical main body portion and the hollow glass body has a second inside diameter at the second end opening. The second inside diameter may be smaller than the first inside diameter. A difference between the first inside diameter and the second inside diameter divided by the first inside diameter may be smaller than 0.02. Alternatively or additionally, the difference between the first inside diameter and the second inside diameter divided by a wall thickness of the cylindrical main body portion may be smaller than 0.2.

Preferred embodiments which can be used with the hollow glass body according to the first embodiment as well as with the hollow glass body according to the second embodiment are described in the following.

The hollow glass body may be a hollow glass body for a medical receptacle or for a non-medical receptacle.

The difference between the first inside diameter and the second inside diameter may be at most 50 μm.

The difference between the first inside diameter and the second inside diameter may be at most 30 μm.

The first inside diameter may be smaller than 28 mm, preferably smaller than 12 mm, preferably smaller than 11 mm, more preferably smaller than 8 mm, more preferably smaller than 7 mm.

The cylindrical main body portion may have an outside diameter that is smaller than 30 mm, preferably smaller than 15 mm, preferably smaller than 10 mm, more preferably smaller than 9 mm.

The cylindrical main body portion may have a wall thickness of between 0.7 mm and 1.5 mm, preferably between 0.7 mm and 1.1 mm.

An inside diameter of the first end opening may be smaller than the second inside diameter.

The inside diameter of the first end opening may be smaller than 5 mm, preferably smaller than 4 mm.

The second end opening may comprise a laser cut area.

The laser cut area may comprise a rounded arch segment that extends from an inside towards an outside of the hollow glass body.

The rounded arch segment may extend annularly around the second end opening.

The difference between the first inside diameter and the second inside diameter divided by the first inside diameter may be smaller than 0.01, preferably smaller than 0.007, more preferably smaller than 0.005.

The difference between the first inside diameter and the second inside diameter difference between the first inside diameter and the second inside diameter divided by a wall thickness of the cylindrical main body portion may be smaller than 0.1, preferably smaller than 0.07, more preferably smaller than 0.05.

The hollow glass body may be a hollow glass body for a medical receptacle.

The hollow glass body may comprise a cone at the side of the cylindrical main body portion opposite the second end opening.

The cone may comprise the first end opening.

The cone may be a syringe cone.

The hollow glass body may be an intermediate product in a manufacturing process for a medical receptacle.

The hollow glass body may be a medical receptacle or a component of a medical receptacle.

The hollow glass body may be a syringe barrel.

The hollow glass body may be a medical cartridge, in particular a drug cartridge.

The hollow glass body may consist of glass of hydrolytic class 1 according to DIN 12111 (ISO 719).

The hollow glass body may consist of borosilicate glass.

A receptacle according to an embodiment may comprise the hollow glass body according to an embodiment.

The receptacle may be a medical receptacle.

The receptacle may further comprise a formulation contained therein.

The formulation may comprise at least one pharmaceutically active substance or a pharmaceutical carrier substance. The pharmaceutical carrier substance may be WFI (Water for Injection).

The medical receptacle may comprise a plug, a syringe piston, or another closure element inserted into an end of the medical receptacle at which the hollow glass body has been separated from the glass tube by laser cutting.

In a use according to the present invention, the hollow glass body is used for preparing a receptacle.

The receptacle may be a medical receptacle.

The use may comprise using the hollow glass body for receiving a formulation comprising at least one pharmaceutically active substance or a pharmaceutical carrier substance. The pharmaceutical carrier substance may be WFI.

A method of manufacturing the hollow glass body according to the present invention comprises laser cutting a glass tube in order to separate the hollow glass body from a glass tube. The laser cutting operation may generate a laser cut around the second end opening.

Hollow glass bodies according to the present invention can be manufactured in an efficient way using laser cutting. Hollow glass bodies according to the present invention can be efficiently handled and further processed by a machine because they have only a slight reduction in the inside diameter at the second end opening.

BRIEF DESCRIPTION OF DRAWINGS

Embodiments of the invention are described in detail with reference to the Figures, in which similar or identical reference signs designate similar or identical elements.

FIG. 6 shows a beam profile in a method and system used for producing a hollow glass body according to the present invention.

FIG. 7 shows a time-dependent output power of a laser beam used for producing the hollow glass body according to the present invention.

DETAILED DESCRIPTION OF EMBODIMENTS

Hollow glass bodies for medical or non-medical receptacles are described in the following with reference to the Figures. Although some embodiments are described in the context of medical receptacles such as syringes or drug cartridges or in the context of specific production methods, the embodiments are not limited thereto. The hollow glass bodies according to the present invention can also be used for non-medical receptacles.

A "hollow glass body for a medical receptacle", as used herein, refers to a hollow glass body that forms a medical receptacle, that is a component of a medical receptacle, or that is an intermediate product for producing a medical receptacle. For example, the hollow glass body may be a syringe or medical cartridge, in particular a drug cartridge, or may be a component of such a medical receptacle. The term "hollow glass body for a non-medical receptacle" can be understood in an analogous manner.

Hollow glass bodies according to embodiments can be separated from a glass tube by means of laser radiation. The separation can be performed using laser sublimation cutting, whereby geometrical characteristics are attainable that are particularly advantageous compared to conventional production methods. In particular, an end of a hollow glass body that has been separated from a glass tube using laser sublimation cutting is distinguished in its shape from an end of a hollow glass body that has been separated from a glass tube by mechanically introducing a starting scratch in combination with subsequent heating by laser radiation and cooling.

Figure 1:
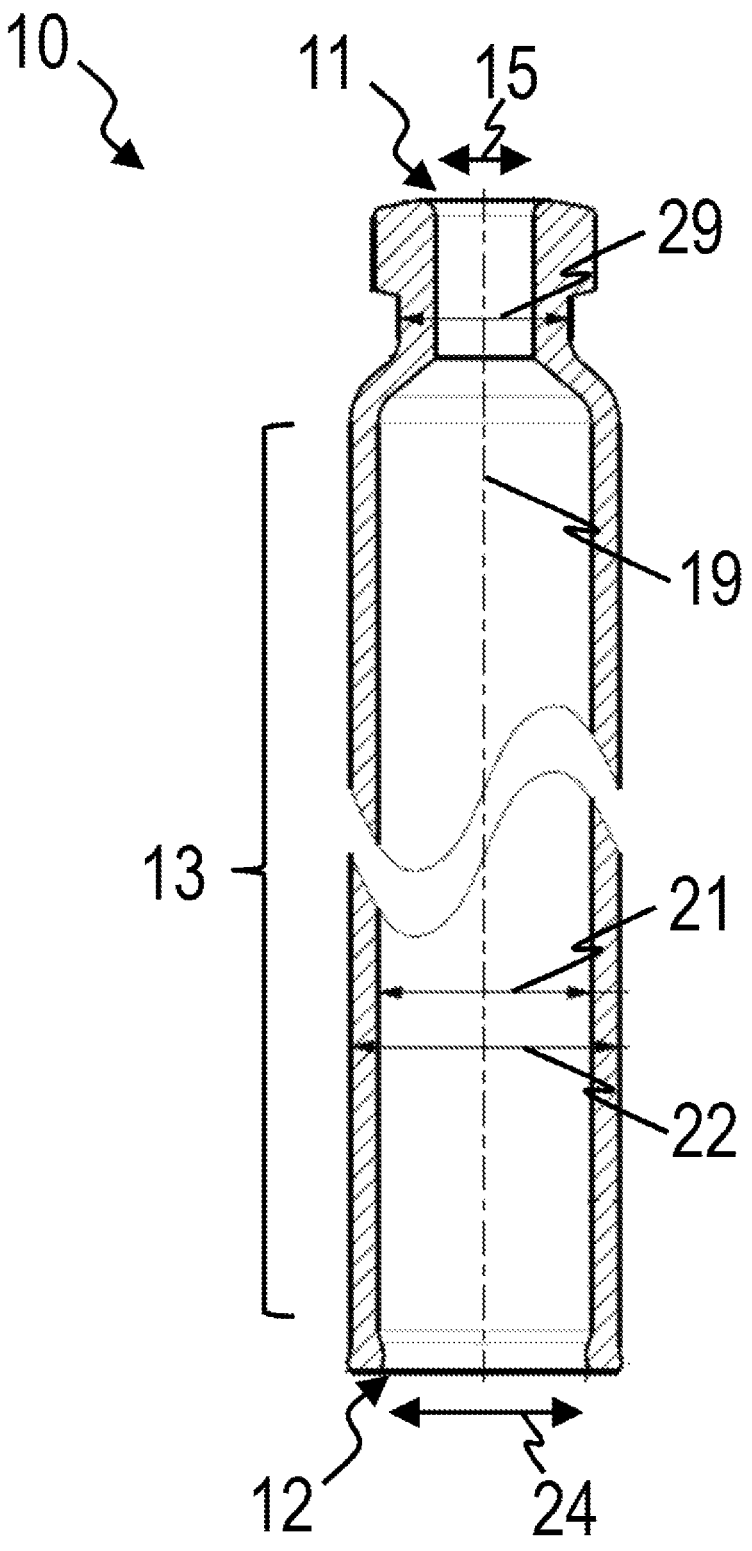
FIG. 1 is a sectional view of a medical receptacle produced with the method and system according to an embodiment.
Figure 2:
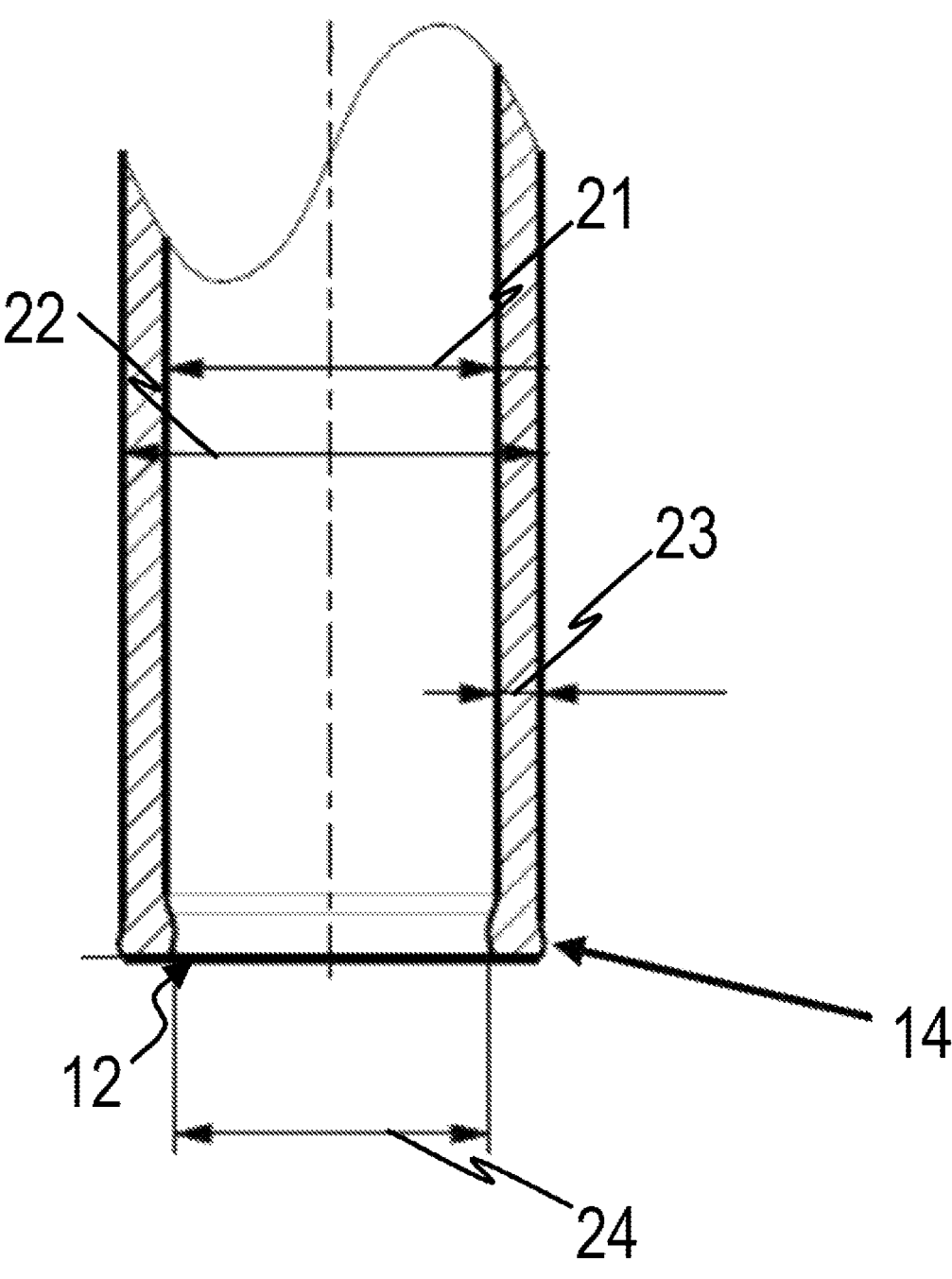
FIG. 2 is a detail view of the medical receptacle of FIG. 1.

FIG. 1 is a sectional view of a hollow glass body 10 according to the present invention. FIG. 2 is a detail view of the hollow glass body 10 of FIG. 1. The hollow glass body 10 may consist of glass of hydrolytic class 1 according to DIN 12111 (ISO 719). The hollow glass body 10 may consist of borosilicate glass.

The hollow glass body 10 may form a medical or non-medical receptacle or may form a component of a medical or non-medical receptacle. The hollow glass body 10 may be a syringe barrel or a medical cartridge.

The hollow glass body 10 has a first end opening 11 and a second end opening 12. The first end opening 11, for example, may be provided on a collar shape in which an outside diameter of the hollow glass body 10 has a constriction 29 or on a syringe cone. An inside diameter 15 of the first end opening 11 may be smaller than 5 mm, preferably smaller than 4 mm.

The hollow glass body 10 has a cylindrical main body portion 13 arranged between the first end opening 11 and the second end opening 12. The hollow glass body 10 may extend rotationally symmetrically about a center axis 19 at least in the cylindrical main body portion 13 and advantageously along its entire length.

In its cylindrical main body portion 13, the hollow glass body 10 may have a first inside diameter 21, an outside diameter 22 and a wall thickness 23. The outside diameter 22 may be smaller than 30 mm, preferably smaller than 15 mm, preferably smaller than 10 mm, more preferably smaller than 9 mm. The first inside diameter 21 in the main body portion 13 (which is referred to as $d_1$ in the following) may be smaller than 28 mm, preferably smaller than 12 mm, preferably smaller than 11 mm, preferably smaller than 8 mm, preferably smaller than 7 mm. The wall thickness 23 may be smaller than 1.5 mm, preferably smaller than 1.1 mm. The wall thickness 23 may be between 0.7 mm and 1.1 mm.

At the second end opening 12, the hollow glass body 10 may have a laser cut 14 which is generated when separating the hollow glass body 10 from a glass tube and which is subsequently not reshaped again.

An inside diameter of the second end opening 12 can be defined as clear width of the hollow glass body 10 at the second end opening 12. If the hollow glass body 10 is not formed so as to be fully rotationally symmetric at the second end opening 12, the second inside diameter $d_2$ at the second end opening 12 can be defined based on a cross-sectional area $A_2$ at the second end opening 12 not covered by the glass of the hollow glass body when viewed along a center axis 19 of the hollow glass body according to $$d_2=[4\ A_2/\pi]^{0.5} \tag{1}$$

In a hollow glass body according to the present invention, the second inside diameter $d_2$ 24 at the second end opening 12 is smaller than the first inside diameter $d_1$ 21 in the main body portion 13.

In contrast to conventional hollow glass bodies produced by using laser radiation, a difference $\Delta$ between the second inside diameter $d_2$ 24 at the second end opening 12 and the first inside diameter $d_1$ 21 in the main body portion 13

$$\Delta=d_2-d_1 \tag{2}$$

is rather small. The difference $\Delta$ may be at most 100 μm, advantageously at most 50 μm, more preferably at most 30 μm in the hollow glass body 10 according to the present invention.

The difference $\Delta$ in relation to the first inside diameter $d_1$ 21 in the main body portion 13

$$\Delta/d_1 \tag{3}$$

can be less than 0.02, preferably less than 0.01, preferably less than 0.007, more preferably less than 0.005.

The difference $\Delta$ in relation to the wall thickness wt of the hollow glass body in the main body portion 13

$$\Delta/wt \tag{4}$$

can be less than 0.2, preferably less than 0.1, preferably less than 0.07, more preferably less than 0.05.

If the hollow glass body 10 is not formed so as to be fully rotationally symmetric in the main body portion 13, the first inside diameter $d_1$ 21 in the main body portion 13 can be defined based on an inside cross-sectional area $A_1$ at a center of the main body portion 13 along the center axis 19 according to $$d_1=[4\ A_1/\pi]^{0.5} \tag{5}$$

A small reduction in the clear width at the second end opening 12 of the hollow glass body 10 formed by a laser cut, as provided in the hollow glass body according to the present invention, entails various advantages. The mechanical handling and further processing, for example when filling the hollow glass body 10 with a formulation and/or closing it, can be simplified. The hollow glass body 10 can be produced efficiently, wherein the hollow glass body 10 can be separated from a glass tube by laser cutting, in particular by laser sublimation cutting, and can optionally be further reshaped.

Figure 3:
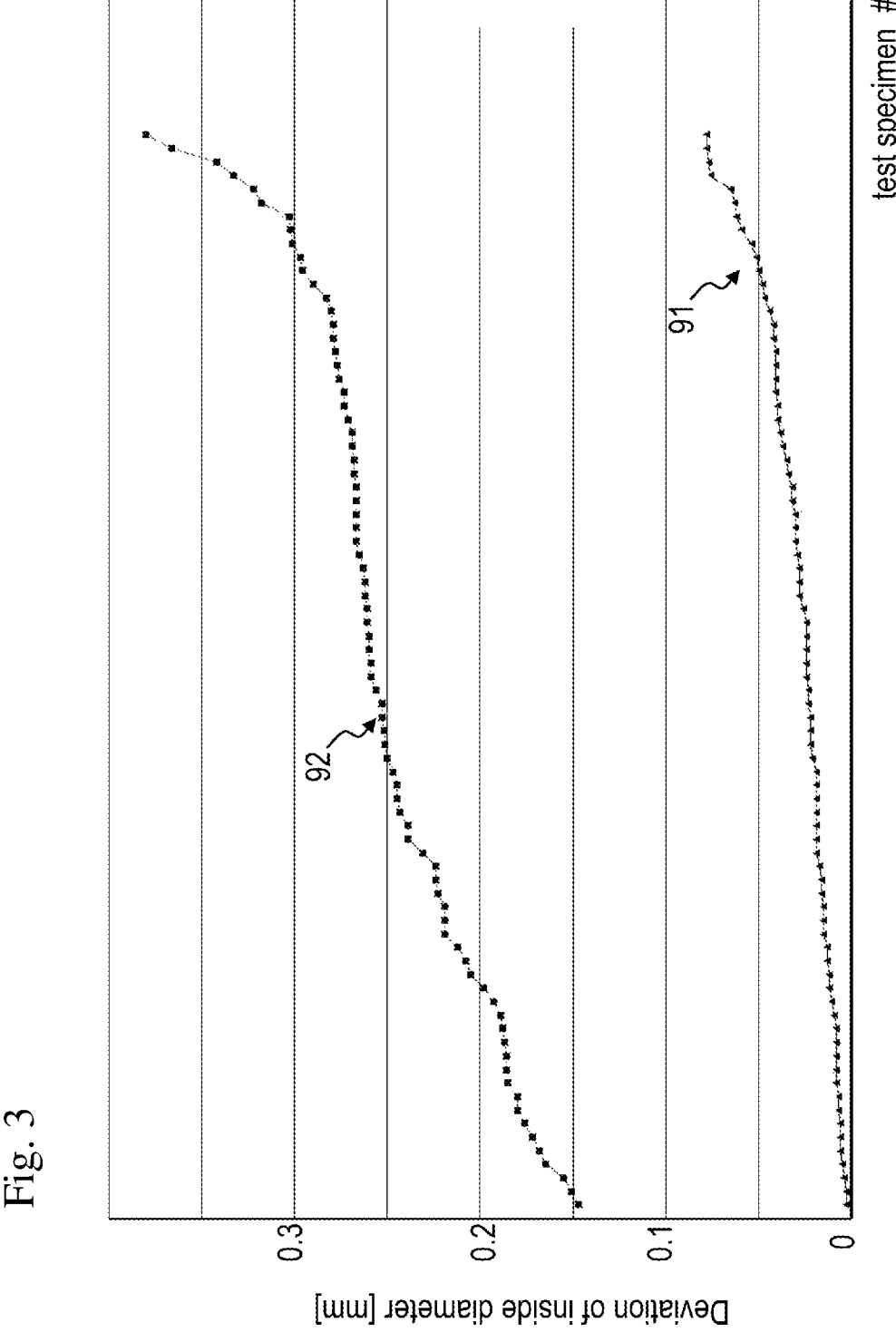
FIG. 3 shows a reduction in inside diameters at an end opening of hollow glass bodies according to the present invention and of conventional hollow glass bodies.

FIG. 3 shows data of inside diameter deviations $\Delta$ measured in a large number of test specimens, which inside diameter deviations correspond to the difference between the first inside diameter in the main body portion and the second inside diameter at the second end opening. In FIG. 3, the inside diameter deviations are plotted as a function of a number of the measured test specimen.

The first data 91 were measured in hollow glass bodies according to the present invention, which have been separated from a glass tube by means of laser sublimation cutting. The second data 92 were measured in conventional hollow glass bodies which were separated from an identical glass tube by means of conventional methods, wherein in the conventional methods a starting scratch was mechanically introduced and the glass tube was subsequently heated by means of laser radiation and cooled again.

Both the first data 91 and the second data 92 were determined for hollow glass bodies each having a first inside diameter of 6.85±0.15 mm and an outside diameter in the cylindrical main body portion of 8.65±0.15 mm. The wall thickness wt of the glass tube from which the hollow glass body was separated and of the main body portion of the separated hollow glass body was 0.9±0.1 mm. The glass tube from which the hollow glass body was separated and the hollow glass body consisted of glass of hydrolytic class 1.

Both the first data 91 and the second data 92 were determined using a $CO_2$ laser having a wavelength of 10.6 micrometers.

The measured inside diameter deviations for the test specimens were sorted in an increasing sequence of inside diameter deviation, both for the hollow glass bodies according to the present invention and the conventional hollow glass bodies. The test specimens were subsequently numbered in a consecutive manner. Thus, the data 91 and the data 92 show monotonously increasing inside diameter deviations which merely reflect the fact that the test specimens have been sorted and numbered according to the inside diameter deviations. What is essential is that the hollow glass bodies according to the invention have inside diameter deviations 91 that are significantly smaller than the inside diameter deviations 92 of the conventional hollow glass bodies.

As can be deduced from FIG. 3, the hollow glass bodies according to the present invention, which have been separated from a glass tube by laser cutting and without mechanically introducing a starting scratch, have an inside diameter deviation $\Delta$ at the end treated with laser radiation which is significantly smaller than in the hollow glass bodies manufactured with conventional methods. In particular, an inside diameter deviation $\Delta$ of less than 0.1 mm, and on average even less than 0.05 mm, can be achieved in the hollow glass bodies according to the present invention.

For the hollow glass bodies according to the invention as represented by the first data 91, the inside diameter deviation Δ divided by the first inside diameter is less than 0.016, on average even less than 0.008.

For the hollow glass bodies according to the invention as represented by the first data 91, the inside diameter deviation Δ divided by the wall thickness in the cylindrical main body portion is less than 0.12, on average even less than 0.06.

Figure 13:
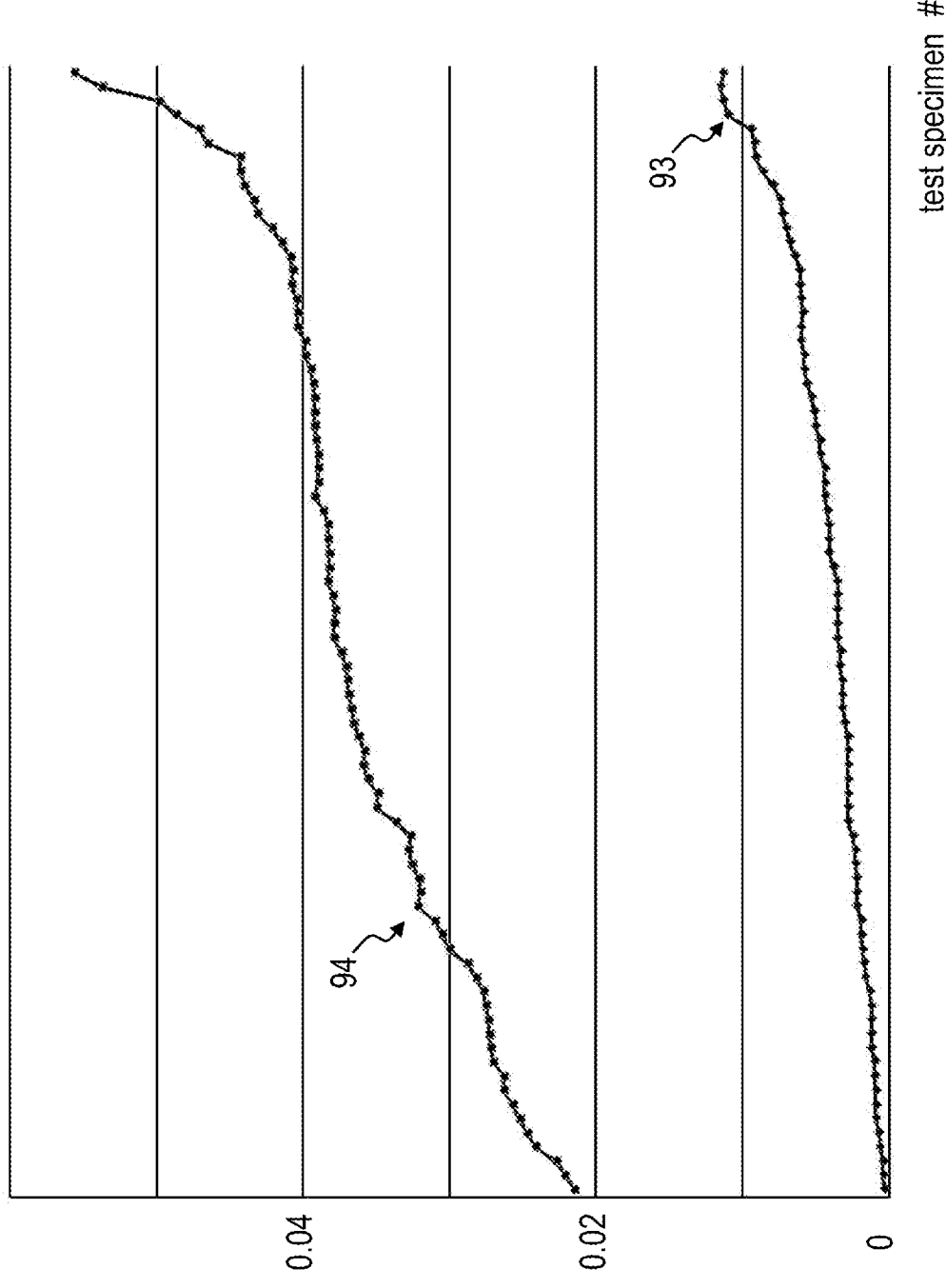
FIG. 13 shows a ratio of the reduction in inside diameter at the end of the separated hollow glass body and a first inside diameter of the hollow glass body for hollow glass bodies according to the present invention and conventional hollow glass bodies.

FIG. 13 shows, in an exemplary manner, the inside diameter deviation Δ divided by the first inside diameter of the respective hollow glass body for the hollow glass bodies of the present invention for which the inside diameter deviation is shown in FIG. 3. The data 93 represent the ratio of the inside diameter deviation Δ and the first inside diameter for the test specimens produced by the method according to the present invention. The data 94 represent the ratio of the inside diameter deviation Δ and the first inside diameter for the test specimens produced by the conventional method described above. The test specimens according to the present invention have a ratio 93 of the inside diameter deviation Δ and the first inside diameter that is less than 0.02. The ratio of the inside diameter deviation Δ and the inside diameter of the cylindrical main body portion can be significantly reduced for hollow glass bodies according to the present invention.

Similarly, hollow glass bodies according to the present invention may have a ratio of the inside diameter deviation Δ and the wall thickness of the cylindrical main portion which is significantly reduced compared to conventional hollow glass bodies.

Figure 4:
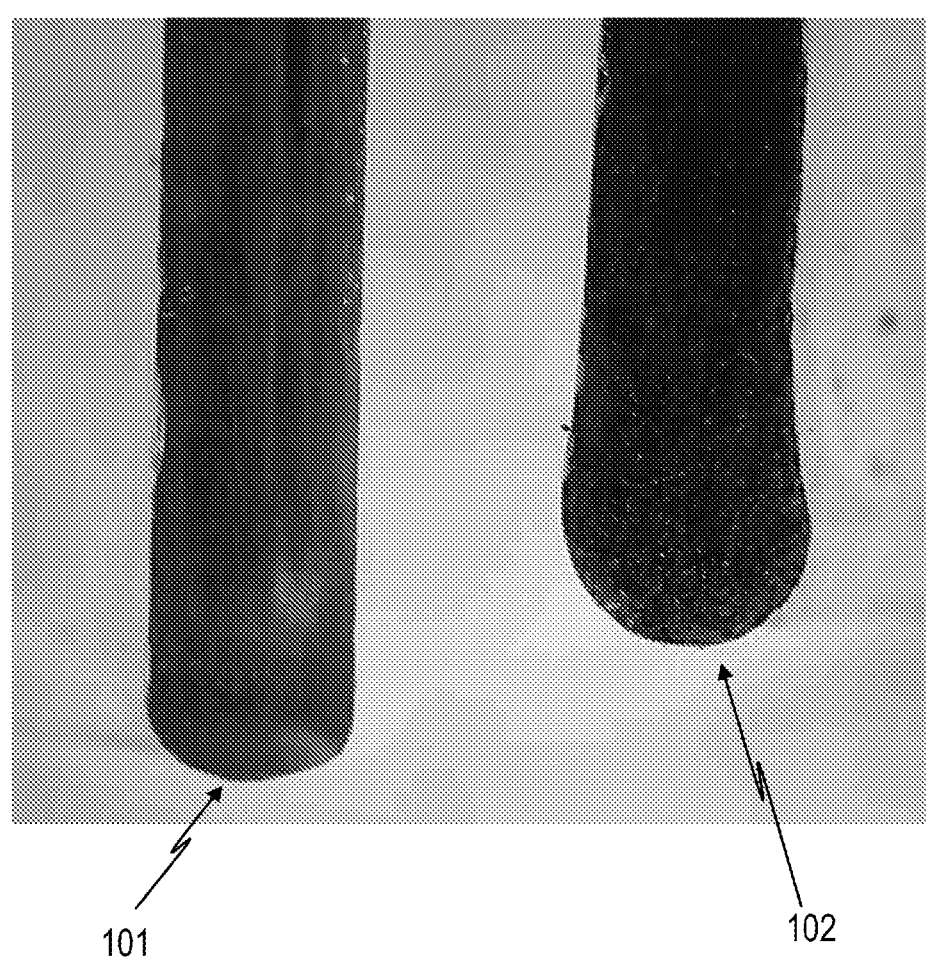
FIG. 4 is a photograph of an end opening of a hollow glass body according to the present invention and of a conventional hollow glass body.

FIG. 4 shows an end 101 of a hollow glass body according to the present invention which has been separated from a glass tube by laser cutting and without mechanically introducing a starting scratch, and an end 102 of a conventional hollow glass tube that has been separated from a glass tube by mechanically introducing a starting scratch and subsequent heating by laser radiation and cooling. While the end 102 of the conventional hollow glass body has a significant bulge at the inner side of the conventional hollow glass body (in FIG. 4 on the right-hand side), the end 101 of the hollow glass body according to the present invention only has a small bulge towards the inner side of the hollow glass body according to the present invention (in FIG. 4 on the left-hand side).

The hollow glass body according to the present invention can be separated from a glass tube by laser cutting to manufacture a medical receptacle. A laser beam used for the laser cutting operation can be focused on a wall of the glass tube.

By focusing the laser beam on a wall of the glass tube, energy densities can be achieved which allow the hollow glass body to be separated even without requiring a scratch to be mechanically introduced. The end of the hollow glass body exposed to the laser beam during separation can have the second inside diameter that is only slightly reduced compared to the first inside diameter of the cylindrical main body portion of the hollow glass body.

The laser beam may be focused so that a focal point of the laser beam is within a wall of the glass tube.

The laser beam may be focused so that on a first side of the glass tube the focal point of the laser beam is within the wall of the glass tube and on an opposite side of the glass tube a laser intensity is no longer sufficient to cut the glass tube. A circumferential laser cut may be generated by a relative movement between the glass tube and the laser beam.

The laser beam may impinge on the wall of the glass tube along a direction transverse to a center axis of the glass tube, in particular perpendicularly to the center axis of the glass tube.

The relative movement between the glass tube and the laser beam may be implemented in various ways:

(1) the glass tube is rotated during the laser cutting, and a beam axis of the laser beam is not moved during the laser cutting;

(2) a beam axis of the laser beam is moved, e.g. rotated in a plane perpendicular to the center axis of the glass tube, during the laser cutting and the glass tube is not rotated during the laser cutting; and (3) a beam axis of the laser beam is moved, e.g. rotated in a plane perpendicular to the center axis of the glass tube, during the laser cutting and the glass tube is rotated during the laser cutting.

The laser cutting operation may comprise laser sublimation cutting. The laser cutting operation may be carried out in such a way that laser sublimation cutting takes place in a first zone located inside the wall of the glass tube, and melting processes may in any case also take place in a second zone in the wall of the glass tube, said second zone surrounding the first zone.

The laser beam may be a pulsed laser beam which comprises a sequence of pulses having a pulse length and a repetition rate. The method may further comprise: controlling the pulse length and repetition rate using an open-loop control or using a closed-loop control in order to cut at least a zone of the wall of the glass tube by laser sublimation cutting.

The laser beam may be focused in such a way that a Rayleigh length of the laser beam is equal to or smaller than a wall thickness wt of the glass tube, preferably equal to or smaller than 0.8×wt, preferably equal to or smaller than 0.6×wt, more preferably equal to or smaller than 0.5×wt.

The hollow glass body may be separated from the glass tube without the mechanical introduction of a scratch.

The hollow glass body may be separated from the glass tube at a separation area without any mechanical force being exerted onto the glass tube.

The method may comprise causing a relative rotation between the laser beam and the glass tube during the laser cutting operation.

The glass tube may have an outside diameter of less than 30 mm, preferably of less than 15 mm.

The glass tube may have an inside diameter of less than 28 mm, preferably of less than 12 mm.

The glass tube may have a wall thickness of less than 1.5 mm, preferably less than 1.1 mm. The glass tube may have a wall thickness of between 0.7 mm and 1.1 mm.

The hollow glass body may be separated from the glass tube in less than 1 s, preferably in less than 0.9 s by means of laser cutting.

The glass tube may consist of glass of hydrolytic class 1 according to DIN 12111 (ISO 719).

The laser beam may comprise pulses with a repetition rate of 3 kHz to 30 kHz, preferably 4 kHz to 12 kHz.

The laser beam may be pulsed and may have a pulse-duty factor of between 5% and 35%, preferably between 8% and 17%.

The laser beam may be generated using a $CO_2$ laser.

The laser beam may have a beam diameter at the laser beam focal point which is from 50 to 250 micrometers, preferably from 100 to 200 micrometers.

The glass tube may be rotated during the laser cutting operation at a speed of more than 100 rpm, preferably between 150 rpm and 700 rpm.

The laser beam may be output from a laser nozzle, from which gas exits at a positive pressure. The positive pressure may be greater than 0.1 bar, preferably greater than 0.3 bar. The glass tube may be accurately aligned on both ends both in an axial direction and in an circumferential direction during the laser cutting operation.

With reference to FIGS. 5 to 12, methods and systems are described in detail which can be used for producing a hollow glass body 10 according to the present invention.

Figure 5:
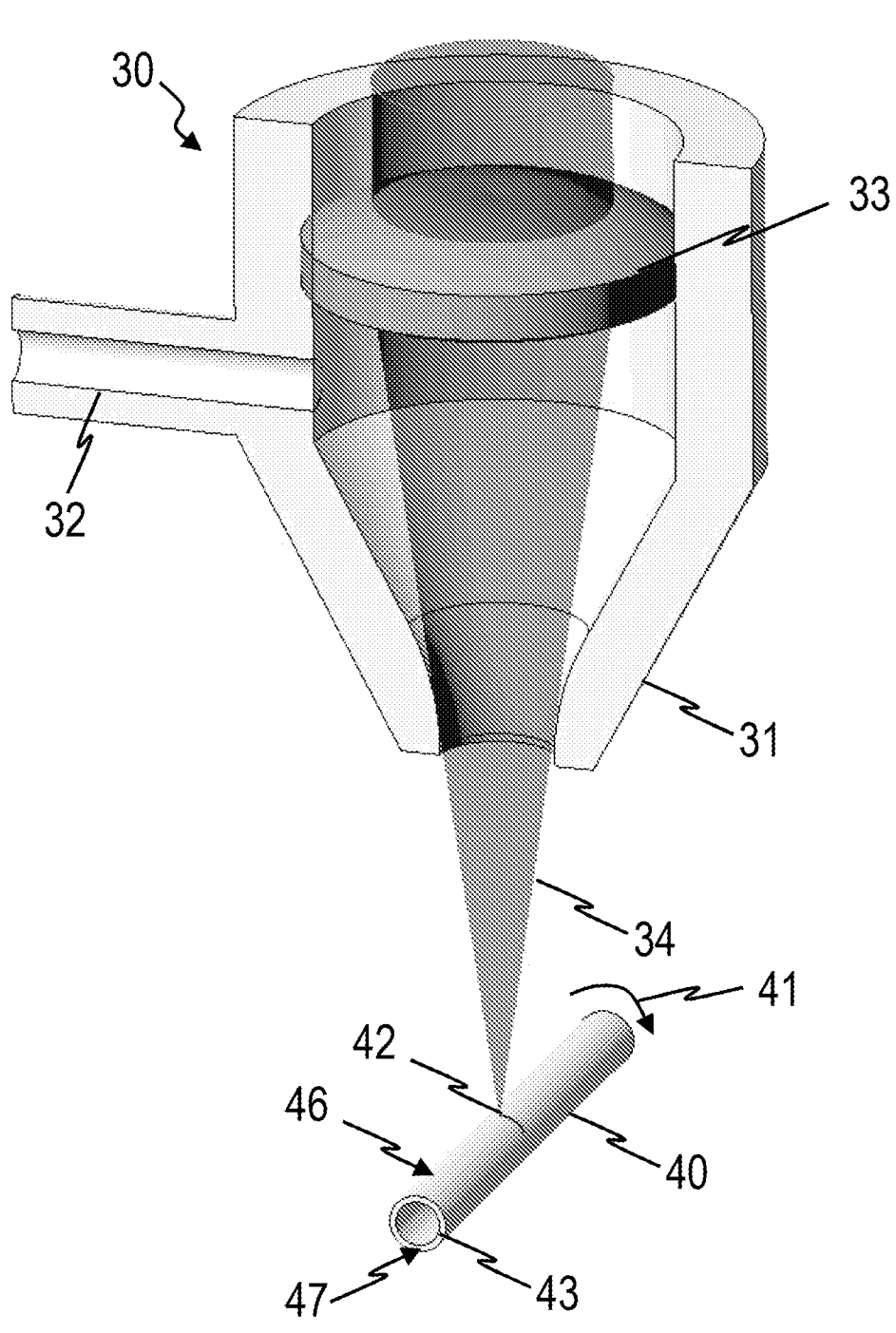
FIG. 5 is a schematic illustration of a laser cutting operation in a method and system used for producing a hollow glass body according to the present invention.

FIG. 5 shows components of a system 30 for separating a hollow glass body according to the present invention from a glass tube 40 by laser cutting. The separation can be carried out without the exertion of mechanical force at a separation area, in particular without the introduction of a starting scratch at the separation area of the glass tube 40. The laser cutting operation may comprise laser sublimation cutting in at least a zone of the glass tube 40.

The glass tube 40 may consist of glass of hydrolytic class 1 according to DIN 12111 (ISO 719). The glass tube 40 may consist of borosilicate glass.

A laser beam 34 is focused by a lens 33 in a laser nozzle 31 on a wall of the glass tube 40. While only one lens 33 is shown in FIG. 5, a lens system that may comprise a plurality of lenses may be used to focus the laser beam 34.

The laser nozzle 31 may comprise a gas passage 32. Pressurized gas can leave the laser nozzle 31 along the same opening as the laser beam 34 collimated by the lens 33. Fumes generated during laser cutting, for example, can be removed by the pressurized gas. The side of the focusing device facing the glass tube during laser cutting, such as a side of the front lens 33 facing the glass tube during laser cutting, can be protected.

The glass tube 40 comprises a wall 43. The wall 43 may extend cylindrically around a center axis of the glass tube 40. The glass tube 40 may be rotated around its center axis during the laser cutting operation in order to produce a circumferential laser cut 42. A rotational axis of the rotation 41 of the glass tube 40 may be perpendicular to a center axis of the laser beam 34.

The laser beam 34 may be focused on the glass tube 40 by the focusing device 33 in such a way that a focal point of the laser beam 34 is arranged on a surface or within a wall thickness on the side 46 of the glass tube 40 facing the focusing device 33. The wall on the opposite side 47 of the glass tube 40 may be spaced apart from the focal point of the laser beam 34. By a rotation 41 of the glass tube 40, the wall 43 may be gradually displaced across the focal point of the laser beam along the circumference of the glass tube 40 to generate a circumferential cut.

For a good laser cutting operation, in particular for a laser cutting operation comprising laser sublimation cutting in at least a zone of the wall 43, a beam profile of the laser beam 34 focused by the focusing device 33 may be adjusted to a wall thickness of the glass tube 40. The adjustment of the beam profile to the wall thickness of the glass tube 40 can be achieved by a suitable selection and/or positioning and/or setting of the focusing device 33.

FIG. 6 shows a beam profile of the laser beam 34 focused by the focusing device 33 and a wall thickness 44 of the wall 43 of the glass tube 40 from which the hollow glass body is separated.

The beam profile is adjusted to the wall thickness 44 such that a Rayleigh length 38 is equal to or smaller than the wall thickness 44 (which is referred to in the following as wt). The Rayleigh length 38 may advantageously be equal to or smaller than 0.8×wt, in particular equal to or smaller than 0.6×wt, in particular equal to or smaller than 0.5×wt.

The Rayleigh length 38 can be defined as the distance along the beam axis 35 between a beam waist, at which the laser beam has a minimum beam diameter along a beam axis 35, and a position at which a radius 37 of the laser beam 43 is √2 times the radius 36 at the beam waist.

For a good laser cutting operation, in particular for a laser cutting operation comprising laser sublimation cutting in at least a zone of the wall 43, a laser source of the laser beam 34 can generate a pulsed laser beam. A repetition rate and/or a pulse-duty factor of the pulsed laser beam may be set so that laser sublimation cutting takes place in at least a zone of the wall 43.

FIG. 7 shows a pulse train 50 of intensity pulses which are generated by a laser source and which may be used to separate the hollow glass body from the glass tube 40 by laser cutting. The pulse train 50 comprises a plurality of pulses each having a length 51. Consecutive pulses are separated by an interval 53 without emission of laser light. A time interval 52 between consecutive rising edges of consecutive pulses of the pulse train 50 is the inverse of the repetition rate. The pulse-duty factor is defined as the duration 51 of a pulse divided by the time interval 52 between consecutive rising pulse edges, which time interval 52 defines the inverse of the repetition rate.

To determine suitable parameters for the repetition rate, the pulse-duty factor and optionally further parameters such as the laser frequency and/or laser power, the following process can be used:

(a) Firstly, a parameter field may be defined which is spanned by a plurality of parameters. The plurality of parameters may comprise the repetition rate, the pulse-duty factor and the laser power. In an exemplary embodiment, the parameter field may be defined by repetition rates of 1 kHz to 200 kHz, a pulse-duty factor of 7% to 50% and a laser power of 0.2 kW to 1 kW.

(b) The parameter field may be tested by selecting points of the parameter field with a step size along the different parameter axes.

(c) Laser cutting is performed with the respective parameters.

(d) The laser cut is evaluated based on quantitative quality criteria such as the change A of the inside diameter at the end of the hollow glass body treated with laser cutting and/or the roundness of the cut edges.

(e) Steps (b) to (d) are repeated with smaller step sizes around the regions of the parameter field which have been identified as particularly suitable in the previous iteration.

In exemplary embodiments, the laser source may be controlled so that a pulse train with a repetition rate of 3 kHz to 30 kHz, preferably of 4 kHz to 12 kHz, and a pulse-duty factor of between 5% and 35%, preferably between 8% and 17%, is generated and used for laser cutting.

The laser cutting operation may comprise laser sublimation cutting. Laser sublimation cutting does not have to extend across the entire wall thickness but may be combined with other laser cutting processes that include melting.

Figure 8:
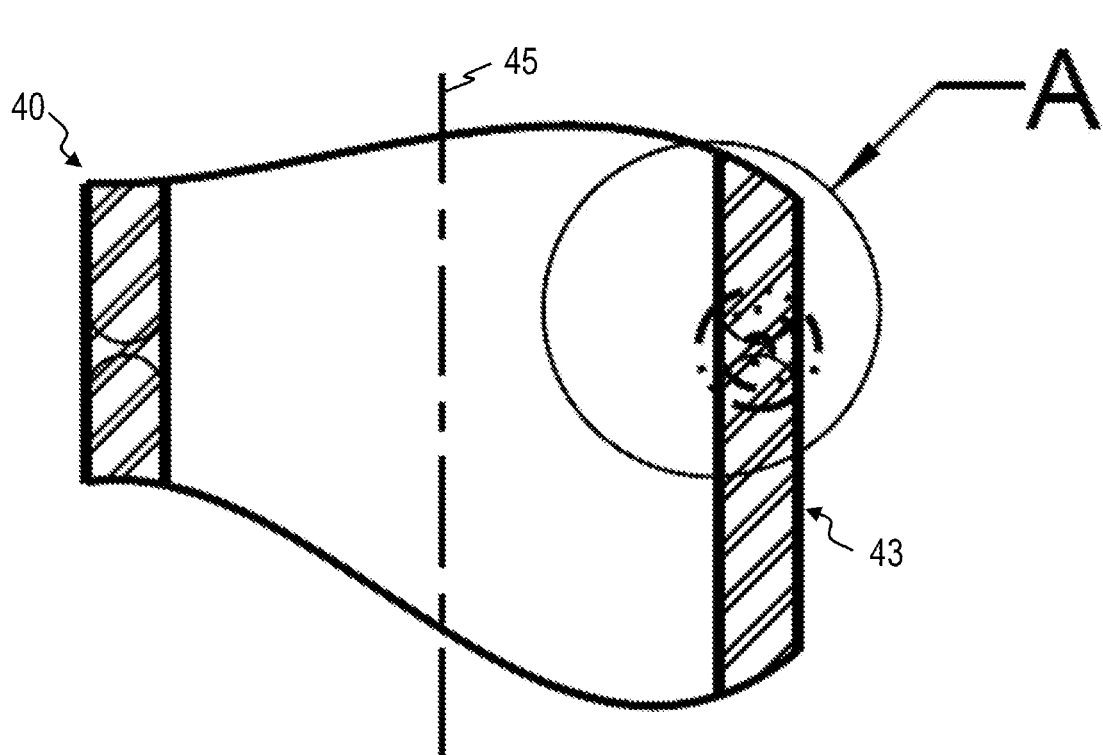
FIG. 8 is a sectional view of a glass tube during the laser cutting operation in a method and system used for producing a hollow glass body according to the present invention.
Figure 9:
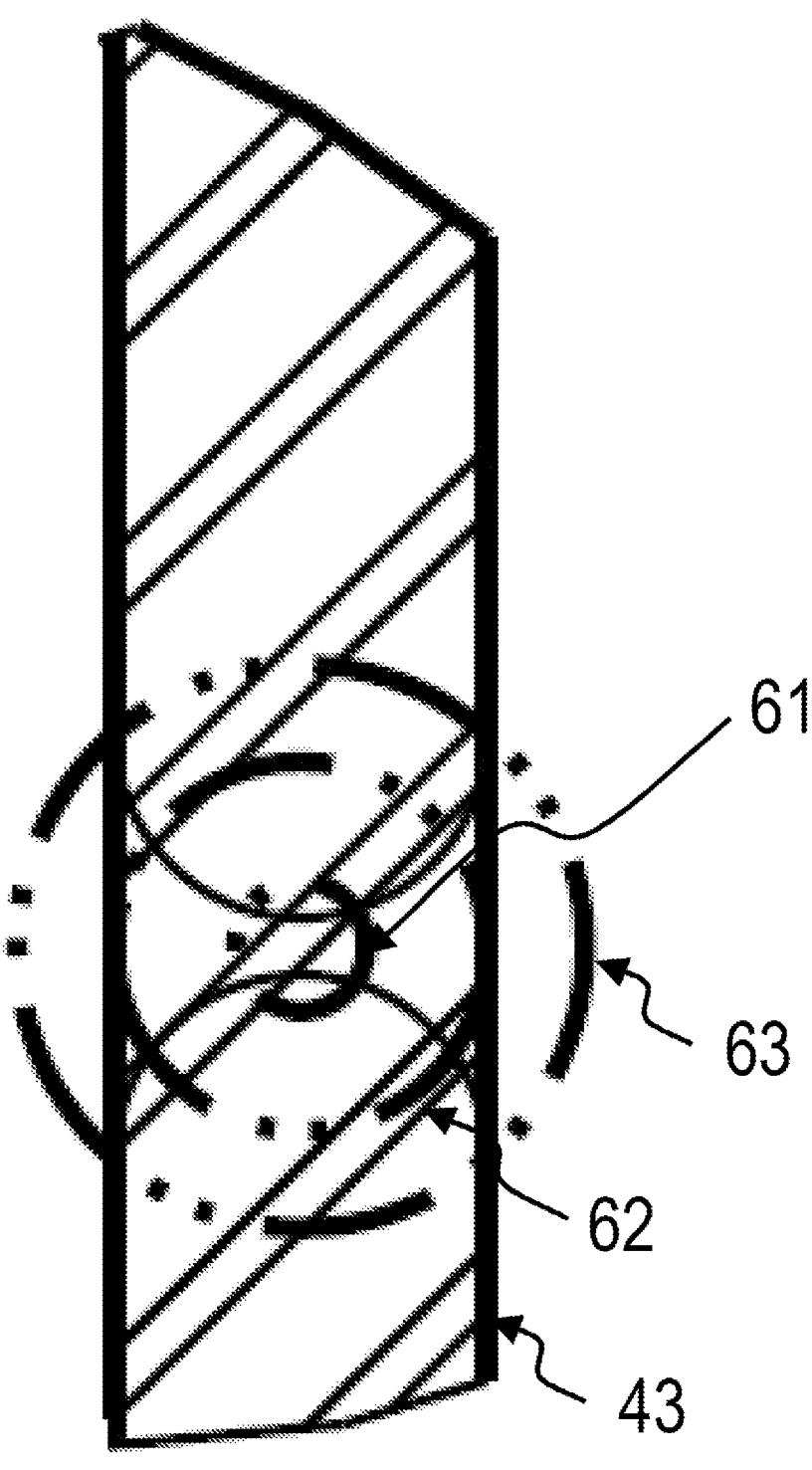
FIG. 9 is an enlarged view of detail A of FIG. 8.

FIG. 8 shows a sectional view of a glass tube 40 to be cut with laser radiation. FIG. 9 shows an enlarged view of detail A marked in FIG. 8.

During laser cutting, the laser beam may be focused on the wall 43 so that the laser beam has a sublimation zone 61 in the center which is aligned concentrically to the beam profile. In the sublimation zone 61, separation by sublimation takes place. In a mixed zone 62 surrounding the sublimation zone 61, the glass of the glass tube 40 is sublimated and melted. The mixed zone 62 is surrounded by a melting zone 63 which generates a radius on the inner and outer surfaces of the wall 43 both on the separated hollow glass body and on the remaining rest of the glass tube, said radius being most clearly visible in FIG. 9. In every sectional plane that includes the center axis of the glass tube 40, the radius forms an arch extending from the inner side to the outer side of the glass tube 40. A tangent of the arch may transition tangentially or approximately tangentially into the inner side and the outer side of the hollow glass body.

The method may be carried out in such a way that the hollow glass body is separated from the glass tube 40 in less than 1 s, preferably in less than 0.9 s by means of laser cutting.

The methods and systems for separating the hollow glass body from a glass tube may be integrated into industrial manufacturing methods in a suitable manner so that a plurality of glass tubes may be efficiently processed.

Figure 10:
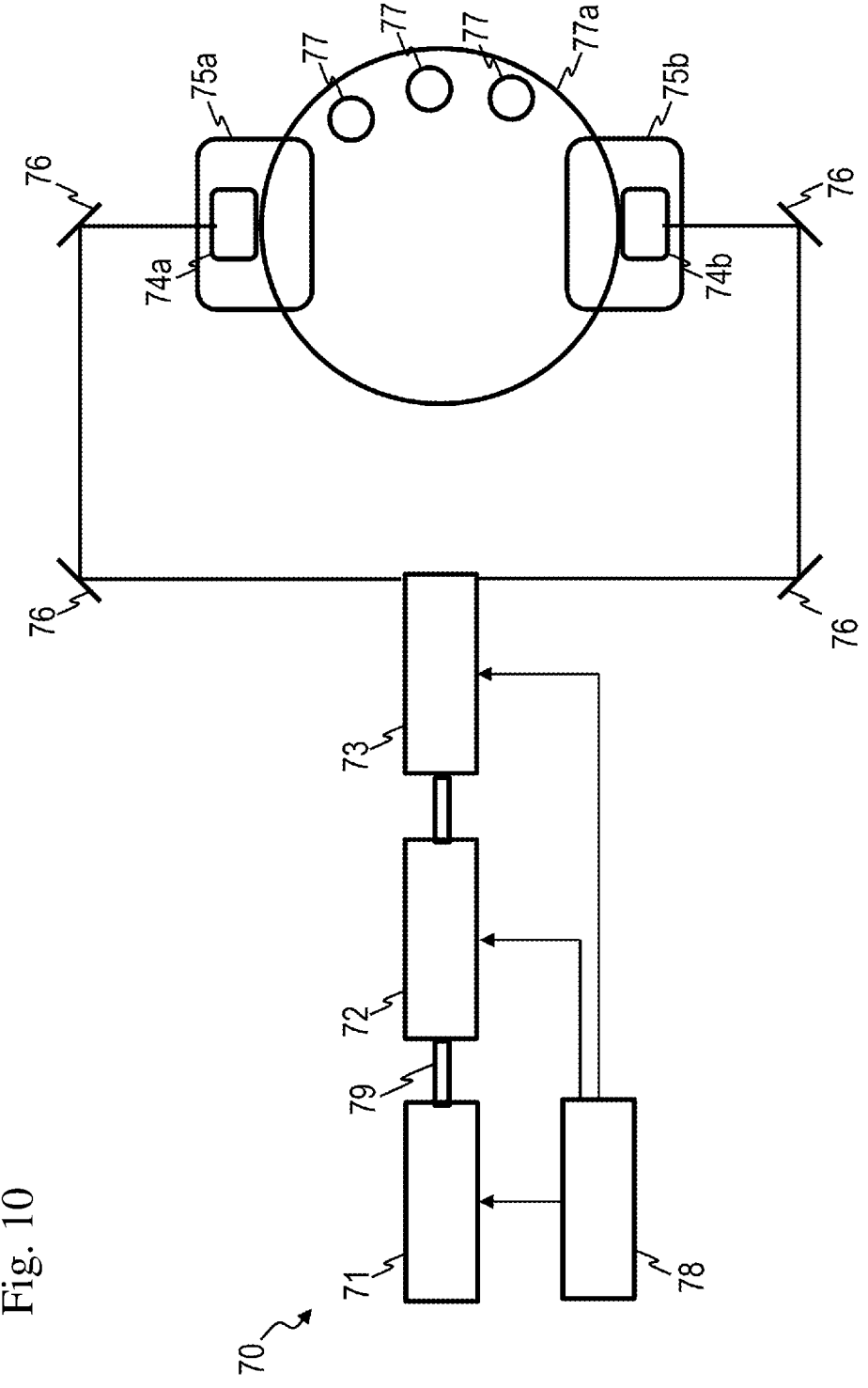
FIG. 10 is a schematic illustration of a system used for producing a hollow glass body according to the present invention.

FIG. 10 is a schematic illustration of a system 70 for manufacturing a hollow glass tube, which may be a medical receptacle or may be the component of a medical receptacle. The system 70 may be configured to separate a hollow glass body from a glass tube by laser cutting. The system 70 may optionally be configured to further reshape the hollow glass body separated from the glass tube and/or to fill and/or to close the reshaped hollow glass body.

The system 70 comprises a laser source 71 and a control device 78. The laser source 71 may be configured to emit a pulsed laser beam. The control device 78 may be configured to control a repetition rate and/or pulse-duty factor of the pulse train using an open-loop control or using a closed-loop control, as described above.

The system 70 may optionally comprise a laser polarizer 72 and/or a laser switch 73. The control device 78 may be configured to control the laser polarizer 72 and/or the laser switch 73 using an open-loop control or using a closed-loop control, for example in order to selectively provide laser radiation 79 to one of a plurality of laser heads 74a, 74b.

The system 70 may comprise a plurality of devices 77, each of which is configured to hold and optionally to rotate a glass tube and only some of which are illustrated in FIG. 8. The devices 77 may rotate the glass tube they are respectively holding while one of the laser heads 74a, 74b performs a laser cutting operation.

The plurality of devices 77 for holding and optionally for rotating a glass tube may be arranged on a conveyor device 77a. The devices 77 may each be rotatably mounted on the conveyor device 77a. The system 70 may comprise a drive device for rotatingly driving the devices 77. The devices 77 may be arranged spaced apart from each other along a circumference of the conveyor device 77a.

The conveyor device 77a may itself be rotatably mounted. The system 70 may comprise a further drive device for rotatingly driving the conveyor device 77a. The drive devices may be controlled by the control device 78 or a separate control device. The drives of the conveyor device 77a and of the devices 77 may be activatable independently of each other.

The laser beam generated by the laser source 71 may be directed to one or more laser heads 74a, 74b via optical components 76, for example mirrors. Each of the laser heads 74a, 74b may have a focusing device as described with reference to FIGS. 5 to 9. Each of the laser heads 74a, 74b may comprise a laser nozzle 31 as described with reference to FIG. 5.

A plurality of laser heads 74a, 74b may be arranged at different positions along the circumference of the conveyor device 77a. The laser heads 74a, 74b may be stationarily mounted in the system 70, but may also comprise mechanically movable components, for example for laser beam tracking. The laser heads 74a, 74b and/or the devices 77 may be configured such that the laser beam emitted by a laser head 74a, 74b for laser cutting is mechanically made to track or follow a respective device 77 when the respective device 77 moves past the laser head 74a, 74b.

The laser heads 74a, 74b may be respectively mounted in safety housings 75a, 75b.

The system 70 may be configured to manufacture a drug cartridge or another medical cartridge. Further processing stations may be arranged along the circumference of the conveyor device 77a. For example, a processing station for reshaping the hollow glass body after the hollow glass body has been separated from the glass tube may be provided. A processing station for filling and/or closing the hollow glass body may be provided.

While FIG. 10 schematically illustrates two laser heads 74a, 74b along the circumference of the conveyor device 77a, it is also possible that only one laser head is provided. It is also possible that more than two laser heads are positioned along the circumference of the conveyor device 77a.

The system 70 may be an index machine in which the conveyor device 77a is repeatedly stopped for laser cutting. The laser heads 74a, 74b may be mounted in a stationary manner.

The system 70 may also be configured such that laser beam tracking is performed during laser cutting while a glass tube is continuously moved past a laser head. Such a configuration will be described in more detail with reference to FIG. 12.

Figure 11:
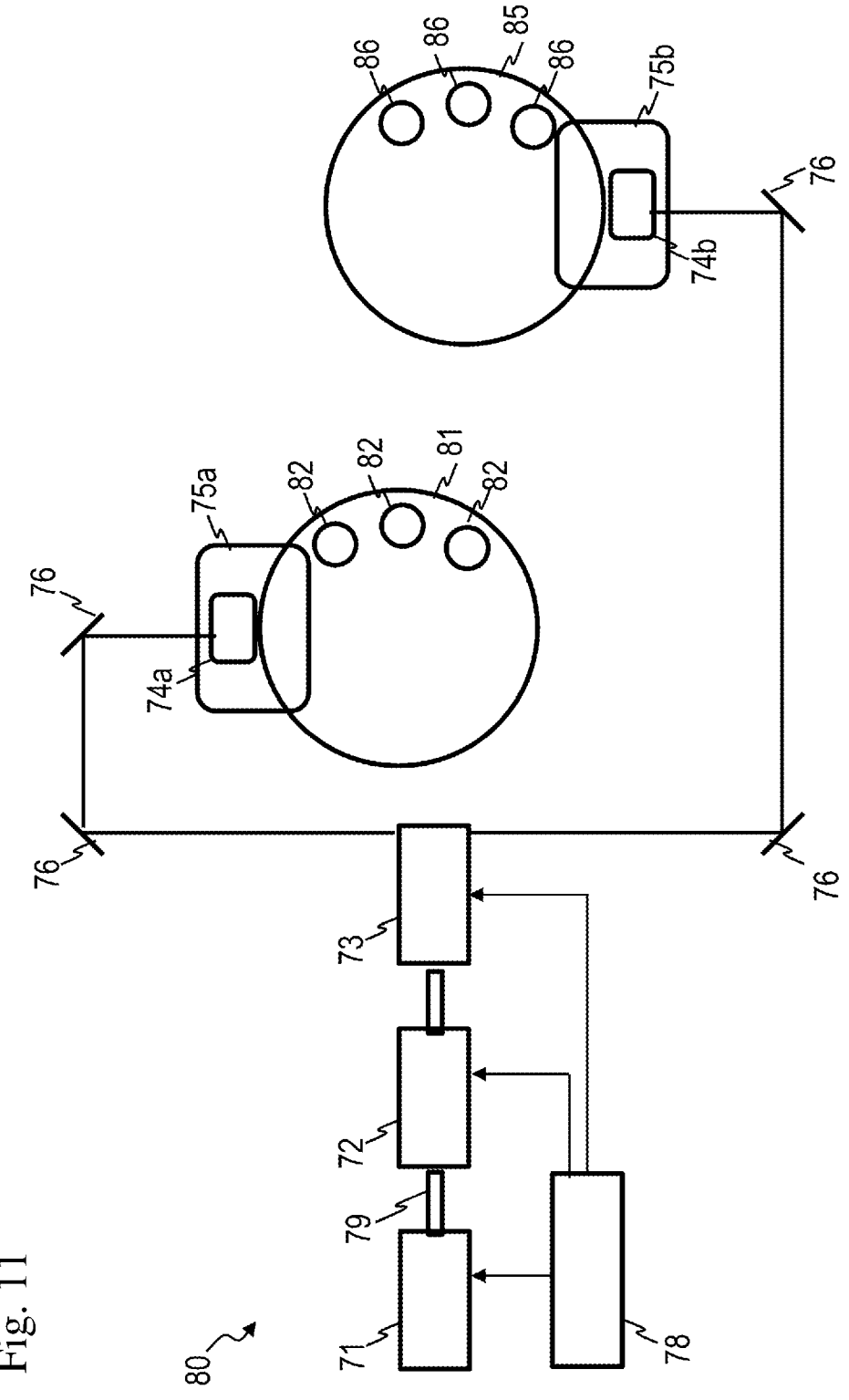
FIG. 11 is a schematic illustration of a system used for producing a hollow glass body according to the present invention.

FIG. 11 is a schematic illustration of a system 80 for manufacturing a hollow glass body, which may be a medical receptacle or may be a component of a medical receptacle. The system 80 may be configured to separate a hollow glass body from a glass tube by laser cutting. The system 80 may optionally be configured to further reshape the hollow glass body separated from the glass tube and/or to fill and/or to close the reshaped hollow glass body.

The system 80 comprises a laser source 71 and a control device 78, which may be configured and designed as described with reference to FIG. 10. A laser polarizer 72, a laser switch 73 and optical components 76 may also be configured as described with reference to FIG. 10.

The system 80 comprises a conveyor device 81 with a plurality of devices 82 positioned thereon for holding and optionally rotating a glass tube. The conveyor device 81 may be rotatingly drivable. Each of the devices 82 may be rotatingly drivable relative to the conveyor device 81. The devices 82 can rotate the glass tube respectively held by them, while a laser head 74a performs a laser cutting operation. The laser head 74a and/or the devices 82 may be configured such that the laser beam emitted by the laser head 74a for laser cutting is mechanically made to track or follow a respective device 82 when the respective device 82 moves past the laser head 74a.

The system 80 comprises a further conveyor device 85 with a plurality of further devices 86 positioned thereon for holding and optionally rotating a glass tube. The further conveyor device 85 may be rotatingly drivable. Each of the further devices 86 may be rotatingly drivable relative to the conveyor device 85. The further devices 86 can rotate the glass tube respectively held by them, while a further laser head 74*b* performs a laser cutting operation. The further laser head 74*b* and/or the further devices 86 may be configured such that the laser beam emitted by the further laser head 74*b* for laser cutting is mechanically made to track or follow a respective one of the further devices 86 when the respective one of the further devices 86 moves past the further laser head 74*b*.

The conveyor device 81 and/or the further conveyor device 85 may each form devices for manufacturing syringes. The system 80 may comprise further stations, which may be positioned on the conveyor device 81 and/or on the further conveyor device 85 to reshape the hollow glass body after the hollow glass body has been separated from the glass tube, to fill the hollow glass body and/or to close the hollow glass body.

The system 80 may be an index machine in which the conveyor devices 81, 85 are repeatedly stopped for laser cutting. The laser heads 74*a*, 74*b* may be mounted in a stationary manner.

The system 80 may also be configured such that laser beam tracking is performed during laser cutting while a glass tube is continuously moved past a laser head. Such a configuration will be described in more detail with reference to FIG. 12.

Figure 12:
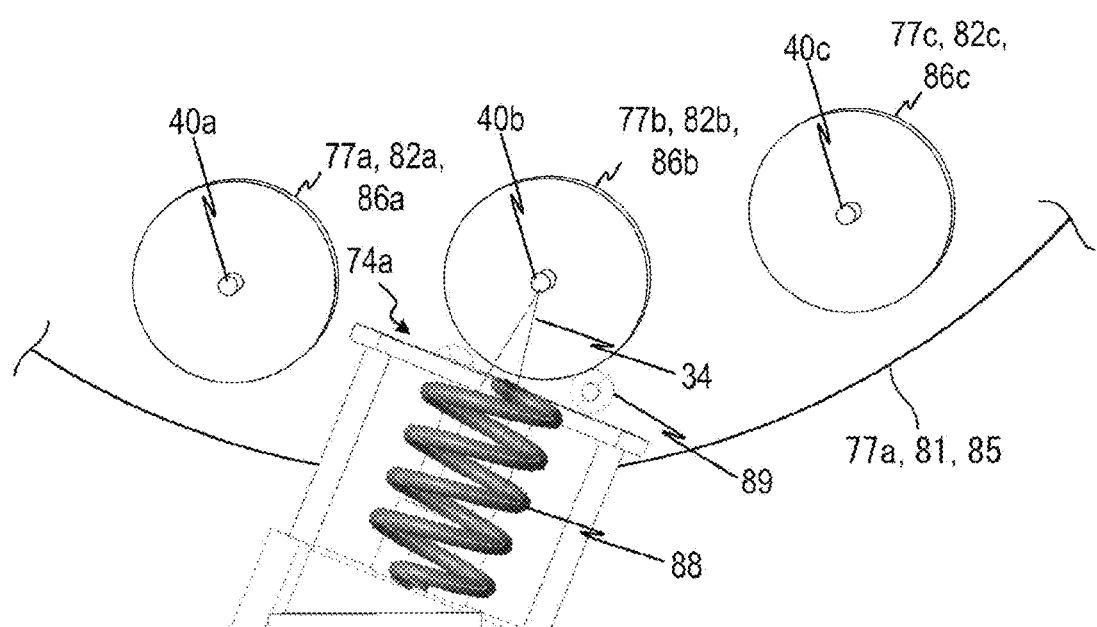
FIG. 12 is an enlarged partial view of components of the systems of FIG. 10 and FIG. 11.

FIG. 12 is an enlarged perspective view of components of the systems 70, 80. The systems 70, 80 comprise a plurality of rotatably mounted devices 77*a-c*, 82*a-c*, 86*a-c*, which may each be arranged on a conveyor device which may be driven independently of the rotatably mounted devices 77*a-c*, 82*a-c*, 86*a-c*. Each of the devices 77*a-c*, 82*a-c*, 86*a-c* may be configured to hold and to rotate a glass tube 40*a*, 40*b*, 40*c*.

A laser head 74*a* may be mounted such that a laser beam 34 is mechanically made to track a respective device 77*a-c*, 82*a-c*, 86*a-c* when the respective device 77*a-c*, 82*a-c*, 86*a-c* is moved past the laser head 74*a*. The laser head 74*a* may be biased by a spring-elastic element 88 towards the devices 77*a-c*, 82*a-c*, 86*a-c*. Rollers 89, a rocker or other tracking members may be provided to mechanically move the laser head when one of the devices 77*a-c*, 82*a-c*, 86*a-c* is moved past the laser head 74*a*.

Various disadvantages associated with conventional hollow glass bodies can be eliminated or mitigated with the hollow glass body according to the present invention. For example, hollow glass bodies for medical receptacles according to the present invention can be manufactured efficiently by laser cutting. Since the inside diameter on the second end opening processed by laser radiation is only slightly smaller than the inside diameter in a cylindrical main body portion, the further mechanical processing, for example during filling with a formulation, is simplified. The risk of damaging the hollow glass body in the production process is reduced compared to conventional methods, in which a significant taper of the hollow glass body at its end can frequently cause an undesired breakage and a resultant standstill of the production machine.

Hollow glass bodies according to embodiments can be used for syringes or drug cartridges without being limited thereto. Hollow glass bodies according to embodiments can also be used as an intermediate product in the production of small bottles or other medical receptacles in which the medical receptacle is open on only one side. Hollow glass bodies according to embodiments may be used for non-medical receptacles or other products.

The invention claimed is:

1. A hollow glass body, comprising:
a cylindrical main body portion having a first inside diameter; and
a first end opening and a second end opening on opposite ends of the hollow glass body, wherein:
the second end opening delimits the cylindrical main body portion and the hollow glass body has a second inside diameter at the second end opening;
the second inside diameter is smaller than the first inside diameter; and
a difference between the first inside diameter and the second inside diameter divided by the first inside diameter is smaller than 0.01.

2. The hollow glass body according to claim 1, wherein the difference between the first inside diameter and the second inside diameter is at most 50 μm.

3. The hollow glass body according to claim 1, wherein the difference between the first inside diameter and the second inside diameter is at most 30 μm.

4. The hollow glass body according to claim 1, wherein the first inside diameter is smaller than 28 mm.

5. The hollow glass body according to claim 4, wherein the first inside diameter is smaller than 12 mm.

6. The hollow glass body according to claim 1, wherein the cylindrical main body portion has an outside diameter that is smaller than 30 mm.

7. The hollow glass body according to claim 6, wherein the outside diameter is smaller than 9 mm.

8. The hollow glass body according to claim 1, wherein a wall thickness of the cylindrical main body portion is between 0.7 mm and 1.1 mm.

9. The hollow glass body according to claim 1, wherein a third inside diameter at the first end opening is smaller than the second inside diameter.

10. The hollow glass body according to claim 9, wherein the third inside diameter is smaller than 5 mm.

11. The hollow glass body according to claim 1, wherein the second end opening comprises a laser cut area.

12. The hollow glass body according to claim 1, wherein the difference between the first inside diameter and the second inside diameter divided by the first inside diameter is smaller than 0.005.

13. The hollow glass body according to claim 1, wherein the difference between the first inside diameter and the second inside diameter divided by a wall thickness of the cylindrical main body portion is smaller than 0.05.

14. The hollow glass body according to claim 1, wherein the hollow glass body is a receptacle, or an intermediate product for manufacturing a receptacle.

15. The hollow glass body according to claim 1, further comprising a cone at a side of the cylindrical main body portion opposite the second end opening.

16. The hollow glass body according to claim 15, wherein the cone comprises the first end opening.

17. The hollow glass body according to claim 15, wherein the cone is a syringe cone.

18. The hollow glass body according to claim 1, wherein the hollow glass body is a syringe barrel.

19. The hollow glass body according to claim 1, wherein the hollow glass body is a medical cartridge.

20. The hollow glass body according to claim 1, wherein the difference between the first inside diameter and the second inside diameter divided by a wall thickness of the cylindrical main body portion is smaller than 0.2.

21. A receptacle, comprising:

the hollow glass body according to claim 1.

22. The receptacle according to claim 21, wherein the receptacle is a medical receptacle.

23. The receptacle according to claim 21, further comprising a formulation which comprises at least one pharmaceutically active substance or a pharmaceutical carrier substance.

* * * * *